(12) United States Patent
Blanche et al.

(10) Patent No.: US 6,518,062 B1
(45) Date of Patent: Feb. 11, 2003

(54) ENZYME COMBINATIONS FOR DESTROYING PROLIFERATIVE CELLS

(75) Inventors: Francis Blanche, Paris (FR); Béatrice Cameron, Paris (FR); Michel Couder, Sucy en Brie (FR); Joël Crouzet, Sceaux (FR)

(73) Assignee: Aventis Pharma S.A., Cedex (FR)

( * ) Notice: Subject to any disclaimer, the term of this patent is extended or adjusted under 35 U.S.C. 154(b) by 0 days.

(21) Appl. No.: 09/125,576
(22) PCT Filed: Mar. 12, 1997
(86) PCT No.: PCT/FR97/00436
§ 371 (c)(1), (2), (4) Date: Sep. 10, 1998
(87) PCT Pub. No.: WO97/35024
PCT Pub. Date: Sep. 25, 1997

(30) Foreign Application Priority Data

Mar. 15, 1996 (FR) .............................. 96 03267

(51) Int. Cl.$^7$ .......................... C12N 15/00; C12N 5/00; C07H 21/04; A01N 63/00; A61K 31/70
(52) U.S. Cl. .................. 435/320.1; 435/69.1; 435/69.7; 435/194; 435/325; 435/455; 536/23.2; 536/23.5; 536/23.4; 424/93.2; 424/93.6; 514/44
(58) Field of Search .............................. 435/320.1, 194, 435/69.1, 69.7, 325, 455; 536/23.2, 23.5, 23.72, 24.1, 23.4; 424/93.2, 93.6; 514/44

(56) References Cited

U.S. PATENT DOCUMENTS 5,877,010 A * 3/1999 Loeb et al. ............... 435/320.1

FOREIGN PATENT DOCUMENTS

| EP | 289229 | 11/1988 |
| WO | WO96/06176 | 2/1996 |
| WO | WO96/16183 | 5/1996 |

OTHER PUBLICATIONS

Anderson, "Human gene therapy", Nature, 392(Suppl.):25–30, Apr. 1998.*
Verma and Somia, "Gene therapy–promises, problems and prospects", Nature, 389:239–242, Sep. 1997.*
Kay et al., "Gene therapy", Proc. Natl. Acad. Sci. USA, 94:12744–12746, Nov. 1997.*
Havenga et al., "Retroviral stem cell gene therapy", Stem Cells, 15:162–179, 1997.*
Chu et al., "Retrovirus–mediated gene transfer into human hematopoietic stem cells", J. Mol. Med., 76:184–192, 1998.*
Fukuchi et al.; Isolation, overexpression and disruption of a Saccharomy ces cerevisiae YNK gene encoding nucleoside diphosphate kinase, 1993, Gene 129: 141–146.*
Tung et. al.; Substrate Specificity of Epstein–Barr Virus Thymidine Kinase, 1994, Antimicrobial Agents and Chemotherapy, 2175–2179.*
Gustafson et al.; The Epstein–Barr Virus Thymidine Kinase Does Not Phosphorylate Ganciclovir or Acyclovir and Demonstrates a Narrow—Type 1 Thymidine Kinase, 1998, Animicrobial Agents and Chemotherapy: 2923–2931.*
Shugar; Viral and Host–Cell Protein Kinase Enticing Antiviral Targets and Relevance of Nucleoside, and Viral Thymidine, Kinases, 1999, Pharmacol. Ther. vol. 82: 3150335.*
Caruso et al., Expression of a Tat–Inducible Herpes Simplex Virus–Thymidine Kinase Gene Protects Acyclovir–Treated CD4 Cells from HIV–1 Spread by Conditional Suicide and Inhibition of Reverse Transcription, Virology 206, 495–503 (1995).
Gentry, Viral Thymidine Kinases and Their Relatives, Pharmac. Ther. 54, 319–355 (1992).

* cited by examiner

Primary Examiner—Scott D. Priebe
Assistant Examiner—Sumesh Kaushal
(74) Attorney, Agent, or Firm—Karen I. Krupen; William C. Coppola

(57) ABSTRACT

Enzyme combinations useful for destroying cells, particularly proliferative cells, are disclosed. In particular, a combination of the following enzymes has been found to enhance the toxicity of nucleoside analogues to proliferating cells: an enzyme that phosphorylates the non-toxic nucleoside analogue to generate a monophosphate analogue, an enzyme that phosphorylates the monophosphate analogue to generate a diphosphate analogue and an enzyme that phosphorylates the diphosphate analogue to generate a toxic triphosphate analogue. Vectors enabling the intracellular expression and transfer of the enzyme combinations, as well as their therapeutic use, particularly in anti-cancer gene therapy, are also disclosed.

25 Claims, 3 Drawing Sheets

SEQUENCE LISTING

<160> NUMBER OF SEQ ID NOS: 11

<210> SEQ ID NO 1
<211> LENGTH: 31
<212> TYPE: DNA
<213> ORGANISM: Saccharomyces cerevisiae

<400> SEQUENCE: 1
gagaagcttg ccatggcccg tcctatcgta a                31

<210> SEQ ID NO 2
<211> LENGTH: 28
<212> TYPE: DNA
<213> ORGANISM: Saccharomyces cerevisiae

<400> SEQUENCE: 2
gaggatccgt ttgacggaag cgacagta                28

<210> SEQ ID NO 3
<211> LENGTH: 30
<212> TYPE: DNA

<213> ORGANISM: Saccharomyces cerevisiae

<400> SEQUENCE: 3
aaggatccac catggctagt caaacagaaa          30

<210> SEQ ID NO 4
<211> LENGTH: 29
<212> TYPE: DNA
<213> ORGANISM: Saccharomyces cerevisiae

<400> SEQUENCE: 4
aagaattcag atcttcattc ataaatcca          29

<210> SEQ ID NO 5
<211> LENGTH: 53
<212> TYPE: DNA
<213> ORGANISM: HSV1

<400> SEQUENCE: 5
ccgggagatg ggggaggcta acggaggtgg cggttctggt ggcggaggct ccg          53

<210> SEQ ID NO 6
<211> LENGTH: 53
<212> TYPE: DNA
<213> ORGANISM: HSV1

<400> SEQUENCE: 6
gatccggagc ctccgccacc agaaccgcca cctccgttag cctcccccat ctc          53

<210> SEQ ID NO 7
<211> LENGTH: 36
<212> TYPE: DNA
<213> ORGANISM: Saccharomyces cerevisiae

<400> SEQUENCE: 7
gagaattccg gaggcggtgg ctcccgtcct atcgta          36

<210> SEQ ID NO 8
<211> LENGTH: 28
<212> TYPE: DNA
<213> ORGANISM: Saccharomyces cerevisiae

<400> SEQUENCE: 8
gaggatccgt ttgacggaag cgacagta          28

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Peptide
      linker for fusing C-terminal sequence of thymidine kinase
      with N-terminal sequence of guanylate
      monophosphate kinase

<400> SEQUENCE: 9

Gly Gly Gly Gly Ser Gly Gly Gly Ser Gly Gly Gly Gly
 1               5                  10

<210> SEQ ID NO 10
<211> LENGTH: 4
<212> TYPE: PRT
<213> ORGANISM: synthetic construct

<400> SEQUENCE: 10

```
Leu Lys Leu Lys
  1

<210> SEQ ID NO 11
<211> LENGTH: 4
<212> TYPE: PRT
<213> ORGANISM: synthetic construct

<400> SEQUENCE: 11

Leu Lys Lys Leu
  1
```

ENZYME COMBINATIONS FOR DESTROYING PROLIFERATIVE CELLS

Figure 1:
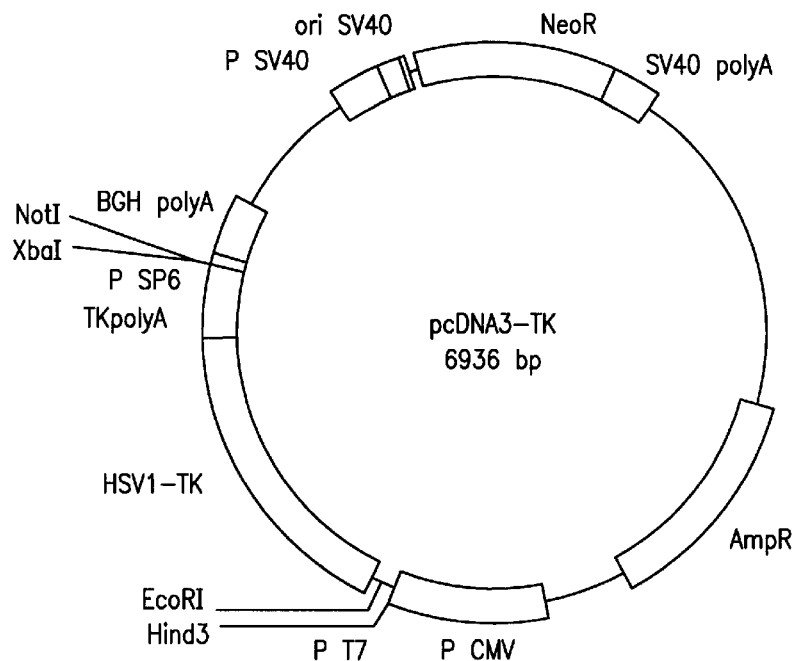

The present invention relates to the field of gene and cell therapy. It relates, in particular, to combinations of enzymes which can be used for the destruction of cells, especially proliferative cells. It also relates to vectors allowing the transfer and intracellular expression of these combinations of enzymes, as well as their therapeutic use, in particular in anticancer gene therapy.

Gene therapy, which consists in introducing genetic information into an organism or a cell, has undergone an extraordinary development over the past few years. The identification of genes involved in pathologies, the development of vectors for the administration of genes, the development of control or tissue-specific expression systems, in particular, have contributed to the development of these new therapeutic approaches. Thus, during the past 5 years, numerous clinical trials of gene or cell therapy have been undertaken in Europe and in the United States, in fields such as monogenic diseases (haemophilia, cystic fibrosis), cancer, cardiovascular diseases or disorders of the nervous system.

In the field of pathologies linked to a cellular hyperproliferation (cancer, restenosis, and the like), various approaches have been developed. Some are based on the use of tumour suppressor genes (p53, Rb), others on the use of antisenses directed against oncogenes (myc, Ras), still others on immunotherapy (administration of tumour antigens or of specific immune cells, and the like). Another approach consists in introducing into the affected cells a toxic or suicide gene capable of inducing the destruction of the said cells. Such genes are, for example, genes capable of sensitizing the cells to a pharmaceutical agent. They are generally genes encoding nonmammalian and nontoxic enzymes which, when they are expressed in mammalian cells, convert a prodrug, which is initially little or nontoxic, to a highly toxic agent. Such a mechanism of activation of prodrugs is advantageous in several respects: it makes it possible to optimize the therapeutic index by adjusting the prodrug concentration or the expression of the enzyme, to interrupt the toxicity by no longer administering the prodrug and to evaluate the mortality rate. In addition, the use of these suicide genes offers the advantage of not being specific to a particular type of tumour, but of general application. Thus, strategies based on the use of tumour suppressor genes or of anti-oncogene antisenses are applicable only to tumours exhibiting a deficiency in the said suppressor gene or an overexpression of the said oncogene. Likewise, approaches based on immunotherapy should be developed on a patient by patient basis to take into account immunorestrictions and immunocompetences. On the other hand, a strategy based on the use of a suicide gene is applicable to any type of tumour, and, more generally, to practically any type of cell.

Numerous suicide genes are described in the literature, such as, for example, the genes encoding cytosine deaminase, purine nucleoside phosphorylase or thymidine kinase, such as for example the thymidine kinases of the varicella virus or herpes simplex virus type 1.

The cytosine deaminase of *Escherichia coli* is capable of catalysing the deamination of cytosine to uracil. The cells which express the *E. coli* gene are therefore capable of converting 5-fluorocytosine to 5-fluorouracil, which is a toxic metabolite (Mullen et al. 1992 Proc. Natl. Acad. USA 89 p33).

The purine nucleoside phosphorylase of *Escherichia coli* allows the conversion of nontoxic analogues of deoxyadenosine to very toxic adenine analogues. As the eukaryotic enzyme does not exhibit this activity, if mammalian cells express the bacterial gene, the analogues of deoxyadenine such as 6-methylpurine-2'-deoxyribonucleoside will be converted to a product which is toxic for these cells (Sorscher et al. 1994 Gene Therapy 1 p233).

The thymidine kinase of the varicella virus allows the monophosphorylation of 6-methoxypurine arabinoside. If mammalian cells express this viral gene, this monophosphate is produced and then metabolized by the cellular enzymes to a toxic compound (Huber et al. 1991 Proc. Natl. Acad. USA 88 p8039).

Among these genes, the gene encoding thymidine kinase (TK) is most particularly advantageous from the therapeutic point of view because, unlike other suicide genes, it generates an enzyme capable of specifically eliminating dividing cells, since the prodrug is converted to a nondiffusible product which inhibits the synthesis of DNA. The viral thymidine kinase, and especially the thymidine kinases of the varicella virus or of the herpes simplex virus type 1, have a substrate specificity different from the cellular enzyme, and it has been shown that they are the target of guanosine analogues such as acyclovir or ganciclovir (Moolten 1986 Cancer Res. 46 p5276). Thus, ganciclovir is phosphorylated to ganciclovir monophosphate only when the mammalian cells produce the HSV1-TK enzyme, then cellular kinases allow the ganciclovir monophosphate to be metabolized to the diphosphate and then to the triphosphate which causes the synthesis of DNA to stop and leads to the death of the cell (Moolten 1986 Cancer Res. 46 p5276; Mullen 1994 Pharmac. Ther. 63 p199). The same mechanism is produced with other thymidine kinases and other guanosine analogues.

Moreover, a propagated toxicity effect ("by-stander" effect) was observed during the use of TK. This effect manifests itself by the destruction not only of the cells which have incorporated the TK gene, but also neighbouring cells. The mechanism of this process may be explained in three ways: i) the formation of apoptotic vesicles which contain phosphorylated ganciclovir or thymidine kinase, obtained from the dead cells, and then phagocytosis of these vesicles by the neighbouring cells; ii) the passage of the prodrug metabolized by thymidine kinase by a process of metabolic cooperation of the cells containing the suicide gene towards the cells not containing it and/or iii) an immune response linked to the regression of the tumour (Marini et al. 1995 Gene Therapy 2 p655).

For persons skilled in the art, the use of the suicide gene encoding the thymidine kinase of the herpes virus is very widely documented. In particular, the first studies in vivo on rats having a glioma show regressions of tumour when the HSV1-TK gene is expressed and when 150 mg/kg doses of ganciclovir are injected (K. Culver et al. 1992 Science 256 p1550). However, these doses are highly toxic in mice (T. Osaki et al. 1994 Cancer Research 54 p5258) and therefore completely proscribed in gene therapy in man.

A number of therapeutic trials are also underway in man, in which the TK gene is delivered to the cells by means of various vectors such as especially retroviral or adenoviral vectors. In clinical trials of gene therapy in man, much smaller doses, of the order of 5 mg/kg, have to be administered and for a short duration of treatment (14 days) (E. Oldfield et al. 1995 Human Gene Therapy 6 p55). For higher doses or for more prolonged treatments, undesirable toxic side effects are indeed observed.

To overcome these disadvantages, it has been proposed to synthesize more specific or more active thymidine kinase derivatives to phosphorylate the guanosine analogues. Thus, derivatives obtained by site-directed mutagenesis have been described. However, no precise biochemical characterization on the pure enzymes has been carried out, no cellular test using these mutants has been published and no functional improvement has been reported (WO 95/30007; Black et al., 1993 Biochemistry 32 p11618). In addition, the inducible expression of an HSV1-TK gene, deleted of its first 45 codons, has been performed in eukaryotic cells, but the prodrug doses used remain comparable to those described in all the trials in the literature (B. Salomon et al. 1995 Mol. Cell. Biol. 15 p5322). Consequently, none of the variants described up until now exhibits an improved activity in relation to thymidine or towards ganciclovir.

The present invention provides an improved method of gene therapy using a suicide gene. The present invention describes, in particular, a method making it possible to improve the efficiency of phosphorylation of the guanosine analogues by thymidine kinases and thereby to improve the therapeutic potential of this treatment. The present invention provides, especially, a method for triphosphorylating nucleoside analogues such as ganciclovir or acyclovir so that the triphosphorylation of these analogues is very significantly increased at ganciclovir doses (resp. acyclovir) i) which are significantly lower; ii) or capable of causing a more pronounced "by-stander" effect; iii) or not leading to a cellular toxicity which might occur when the wild-type thymidine kinase is overexpressed.

This method may be applied to cancer, to cardiovascular diseases, or to any application requiring the death of certain cells such as cells infected with a virus; this virus may be a virus of the HIV (human immunodeficiency virus), CMV (cytomegalovirus) or RSV (respiratory syncytial virus) type.

The present invention is based, in particular, on the use of a combination of enzymes which make it possible to improve, in vivo, the reaction of phosphorylation of the nucleoside analogues.

A first subject of the invention therefore consists in a composition comprising:

an enzyme capable of phosphorylating a nucleoside analogue, to generate a monophosphate analogue, an enzyme capable of phosphorylating the said monophosphate analogue, to generate a diphosphate analogue, and, an enzyme capable of phosphorylating the said diphosphate analogue, to generate a toxic triphosphate analogue.

More particularly, the enzyme capable of phosphorylating a nucleoside analogue, to generate a monophosphate analogue is a thymidine kinase, the enzyme capable of phosphorylating the said monophosphate analogue, to generate a diphosphate analogue is a guanylate kinase and the enzyme capable of phosphorylating the said diphosphate analogue to generate a triphosphate analogue is a nucleoside diphosphate kinase. Moreover, the compositions according to the invention may comprise, not the enzyme directly, but a nucleic acid encoding the enzyme. In this regard, the subject of the invention is also a composition which can be used for the delivery and production in vivo of a combination of enzymes, comprising:

a first nucleic acid encoding an enzyme capable of phosphorylating a nucleoside analogue, to generate a monophosphate analogue, a second nucleic acid encoding an enzyme capable of phosphorylating the said monophosphate analogue, to generate a diphosphate analogue, and, a third nucleic acid encoding an enzyme capable of phosphorylating the said diphosphate analogue, to generate a toxic triphosphate analogue.

Advantageously, the first nucleic acid encodes a thymidine kinase, the second nucleic acid encodes a guanylate kinase and the third nucleic acid encodes a nucleoside diphosphate kinase.

The nucleoside analogue is generally a guanosine analogue, such as for example ganciclovir, acyclovir or penciclovir. Other nucleoside analogues are for example compounds of the trifluorothymidine, 1-(2-deoxy-2-fluoro-beta-D-arabinofuranosyl)-5-iodouracil, ara-A, 1-beta-D-arabinofuranosylthymidine (araT), 5-ethyl-2'-deoxyuridine, iodouridine, AZT, AIU, dideoxycytidine, AraC and bromovinyldeoxyuridine (BVDU) type. The preferred analogues are ganciclovir, acyclovir, penciclovir and BVDU, preferably ganciclovir and acyclovir. The triphosphate form is toxic in the sense that it causes, directly or indirectly, cell death.

When mammalian cells, modified to express thymidine kinase (HSV1-TK for example), are exposed to a nucleoside analogue (ganciclovir for example), they become capable of carrying out the phosphorylation of the ganciclovir to give ganciclovir monophosphate. Subsequently, cellular kinases allow this ganciclovir monophosphate to be metabolized successively to the diphosphate and then the triphosphate. The gancyclovir triphosphate thus generated then produces toxic effects by becoming incorporated into the DNA and partly inhibits the cellular alpha DNA polymerase, thereby causing DNA synthesis to stop and therefore leads to the death of the cell. In this mechanism, the step of monophosphorylation of the nucleoside analogue is considered to be the limiting step. It is for this reason that different approaches have been described in the prior art to try to improve the intrinsic properties of thymidine kinase (creation of TK mutants, research for more efficient administration and expression systems, and the like).

The present invention shows clearly that it is possible to improve the efficacy of the treatment by administering, in combination with a thymidine kinase, other enzymes involved in the phosphorylation of nucleoside analogues. The subject of the present invention is thus various combinations of enzymes which make it possible to optimize the intracellular reaction of triphosphorylation of nucleoside analogues. Another aspect of the present invention relates to vectors allowing the introduction and intracellular expression of these combinations of enzymes. They may be in particular several vectors each allowing the production of an enzyme, or of one or more vectors each allowing the production of several enzymes or of all the enzymes. The present invention also relates to a process for the triphosphorylation of nucleoside analogues in the presence of a combination of enzymes, optionally produced in situ by expression of corresponding genes, as well as a process for the destruction of proliferative cells.

The phosphorylation of the nucleoside monophosphates to the nucleoside triphosphates and then to the triphosphates has been documented in vitro. These phosphorylations are carried out in the presence i) of human erythrocyte lysate in the case of ganciclovir (Cheng et al. 1983 J. Biol. Chem. 258 p12460) or ii) of enzymatic preparations of guanylate kinase and of nucleoside diphosphate kinase of human erythrocytes, in the case of ganciclovir and of acyclovir (Miller et al. 1980 J. Biol. Chem. 255 p720; Smée et al. 1985 Biochem. Pharmac. 34 p1049). Although the phosphorylation of the nucleoside monophosphates to the diphosphates and then to the triphosphates has been demonstrated in mammalian cells, these conversions do not appear to be total with ganciclovir monophosphate or acyclovir monophosphate (Agbaria et al. 1994 Mol. Pharmacol. 45 p777; Caruso et al. 1995 Virology 206 p495; Salomon et al. 1995 Mol. Cell. Biol. 15 p5322).

The present application now describes compositions which make it possible to improve the therapeutic efficacy of a thymidine kinase in vivo.

The first enzyme used in the compositions and methods according to the invention, which is capable of phosphorylating a nucleoside analogue to generate a monophosphate analogue, is advantageously a nonmammalian thymidine kinase. It is preferably a thymidine kinase of viral, and in particular herpetic, origin. Among the herpetic thymidine kinases, there may be mentioned especially the herpes simplex virus type 1 thymidine kinase (HSV1-TK), the herpes simplex virus type 2 thymidine kinase (HSV2-TK), the varicella virus thymidine kinase (VZV-TK), the Epstein-Barr virus thymidine kinase (EBV-TK), or alternatively the thymidine kinase of herpetic viruses of bovine origin (Mittal et al., J. Virol 70 (1989) 2901), equine origin (Robertson et al., NAR 16 (1988) 11303), feline origin (Nunberg et al., J. Virol. 63 (1989) 3240) or simian origin (Otsuka et al., Virology 135 (1984) 316).

The sequence of the gene encoding the thymidine kinase enzyme of the herpes simplex virus type 1 has been described in the literature (see especially McKnight 1980 Nucl. Acids Res. 8 p5931). Natural variants of it exist, leading to proteins having a comparable enzymatic activity on thymidine, or ganciclovir (M. Michael et al. 1995 Biochem. Biophys. Res. Commun 209 p966). The sequence of the gene encoding the thymidine kinase enzyme of the herpes simplex virus type 2 has also been described (Swain et al., J. Virol. 46 (1983) 1045).

The thymidine kinase used in the present invention may be a native thymidine kinase (the naturally occurring form of the enzyme or one of its naturally occurring variants), or a derived form, that is to say resulting from structural modification(s) of the native form. As indicated above, various mutants or derivatives have been described in the literature. Although their intrinsic properties do not appear to be significantly modified, these molecules may be used within the framework of the present invention. They are for example mutants having a modification close to the DRH region of the site of interaction of a nucleoside (WO 95/30007). The DRH region corresponds to the aspartic, arginine and histidine residues at positions 163, 164 and 165 of TK. These three positions are highly conserved between the herpetic TKs. Various mutants have been described at positions 160–162 and 168–170 (WO 95/30007). Other artificial variants possess a modification at the ATP-binding site (FR96 01603). Moreover, other TK derivatives may be prepared according to conventional molecular biology techniques, and used in the combinations of the invention. These mutants may be prepared, for example, by mutagenesis on a nucleic acid encoding a native, preferably herpetic, thymidine kinase or one of its variants. Numerous methods which make it possible to perform the site-directed mutagenesis or the random mutagenesis are known to persons skilled in the art and there may be mentioned the PCR- or oligonucleotide-directed mutagenesis, random mutagenesis in vitro by chemical agents such as for example hydrolylamine or in vivo in mutant E. coli strains (Miller "A short course in bacterial genetics", Cold Spring Harbor Laboratory, Cold Spring Harbor, N.Y., 1992). The sequences thus mutated are then expressed in a cellular or acellular system and the expression product is tested for the presence of a thymidine kinase type activity, under the conditions described especially in the examples. Any enzyme resulting from this process, which has the capacity to phosphorylate a nucleoside analogue, to generate a monophosphate analogue, may be used in the present invention.

Preferably, a TK derived from the herpes simplex virus type 1 thymidine kinase (HSV1-TK) or a corresponding coding nucleic acid is used within the framework of the present invention. It is more particularly HSV1-TK or one of its variants, such as the naturally occurring variants or the artificial variants. Among the artificial variants, there may be mentioned more particularly the variants P155A/F161V and F161I (Biochemistry 32 (1993) p.11618), the variant A168S (Prot. Engin. 7 (1994) p.83) or the variants having a modification at the ATP-binding site, such as the variant M60I. Still more preferably, a nucleic acid encoding the herpes simplex virus type 1 thymidine kinase (HSV1-TK) is used.

The second enzyme used in the compositions and methods according to the invention, which is capable of phosphorylating a nucleoside monophosphate analogue to generate a diphosphate analogue, is advantageously a guanylate kinase. The guanylate kinase (GMPK) was purified from various organisms (man, rat, bovine, yeast). The gene encoding GMPK has also been cloned into various cell types, and especially into the yeast Saccharomyces cerevisiae, GUK1 gene (M. Konrad 1992 J. Biol. Chem. 267 p25652). From this gene, the 20 kDa GMPK enzyme has also been purified. The GMPK gene, designated gmk, has also been isolated and overexpressed in Escherichia coli (D. Gentry et al. 1993 J. Biol. Chem. 268 p14316). This enzyme is different from the S. cerevisiae enzyme in terms of cooperativity and of oligomerization, whereas the sequences exhibit strong regions of identity, 46.2% on 182 residues. The A11042 sequence, identified as encoding a factor having a haematopoietic cell growth potential activity (EP0,274,560), exhibits 51.9% identity on 180 residues with the S. cerevisiae GUK1 gene and appears to constitute the human homologue of GMPK, although no biochemical data has been published.

The third enzyme used in the compositions and methods according to the invention, which is capable of phosphorylating a nucleoside diphosphate analogue to generate a triphosphate analogue, is advantageously a nucleoside diphosphate kinase. Nucleoside diphosphate kinase (NDPK) is an enzyme with a broad substrate specificity and has been purified from a wide variety of sources (M. Inouye et al. 1991 Gene 105 p31). For various organisms (Myxococcus xanthus, Drosophila melanogaster, Dictyostelium discoideum, rat, bovine, man, E. coli and S. cerevisiae), the gene encoding NDPK has been cloned and the corresponding enzymes are highly homologous (K. Watanabe et al. 1993 Gene 29 p141). However, only the higher eukaryotic enzymes possess a "leucine zipper" sequence. The human genes described which encode an NDPK activity are in particular nm23-H1 and nm23-H2. It is suggested that the nm23-H2 gene encodes a bifunctional protein with two independent functions which are NDPK activity and transcription factor (E. Postel et al. 1994 J. Biol. Chem. 269 p8627). The S. cerevisiae YNK gene is not an essential gene for the yeast and encodes NDPK which is probably a tetrameric protein in which the molecular weight of the monomers is 19 kDa (A. Jong et al. 1991 Arch. Biochem. Biophys. 291 p241).

The nucleic sequences encoding the GMPK or NDPK used within the framework of the invention may be of human, animal, viral, synthetic or semisynthetic origin.

In general, the nucleic sequences of the invention may be prepared according to any technique known to persons skilled in the art. By way of illustration of these techniques, there may be mentioned especially:

chemical synthesis, using the sequences described in the literature and, for example, a nucleic acid synthesizer, the screening of libraries by means of specific probes, especially as described in the literature, or alternatively mixed techniques including chemical modification (extension, deletion, substitution and the like) of sequences screened from libraries.

Advantageously, the nucleic sequences used within the framework of the invention are cDNA or gDNA sequences. The cDNA sequences are intron-free sequences obtained from RNA. The gDNA sequences are chromosome regions. In eukaryotes, they comprise one or more introns. The gDNA sequences used within the framework of the invention may comprise all or part of the is introns present in the naturally occurring gene, or one or more introns artificially introduced into a cDNA in order to increase for example the efficiency of expression in mammalian cells. The nucleic acids may encode the native enzymes or variants or derivatives having an activity of the same type. These analogous nucleic acids may be obtained by conventional molecular biology techniques, which are well known to persons skilled in the art. These may be mutagenesis, site-directed or otherwise, hybridization from libraries, deletion or insertion, construction of hybrid molecules and the like. Generally, the modifications affect at least 20% of the bases of the nucleic acid. The functionality of the analogous nucleic acids is determined as described in the examples by assaying the enzymatic activity of the expression product.

A specific composition for the purposes of the invention comprises a first nucleic acid encoding a thymidine kinase and a second nucleic acid encoding a nucleoside diphosphate kinase. In this embodiment, the nucleoside diphosphate kinase is preferably of nonhuman eukaryotic origin. Nonhuman enzyme is understood to mean an enzyme not naturally present in human cells. It may be a viral or animal enzyme, or derived from a lower eukaryotic organism (such as a yeast). It may also be a non-naturally occurring derivative of a human enzyme, exhibiting one or more structural modifications. More preferably, the NDPK used in the present invention is chosen from yeast or bovine NDPK. These compositions may, in addition, comprise a nucleic acid encoding a guanylate kinase, such as, for example, a yeast guanylate kinase.

Another specific composition for the purposes of the invention comprises a first nucleic acid encoding a thymidine kinase and a second nucleic acid encoding a nonhuman guanylate kinase. The nonhuman GMPK may be chosen from rat, bovine, yeast or bacterial GMPK, or derivatives thereof. Preferably, the GMPK is derived from a low eukaryote, especially yeast.

According to a particularly advantageous embodiment, the nucleoside diphosphate kinase used within the framework of the present invention is of eukaryotic or animal origin. Still more preferably, it is a yeast or bovine nucleoside diphosphate kinase. The applicant has, indeed, demonstrated that, surprisingly, the nucleoside diphosphate kinase from yeast, and especially from *Saccharomyces cerevisiae* or that from bovines, made it possible to phosphorylate nucleoside diphosphate analogues, such as ganciclovir diphosphate or acyclovir diphosphate, to nucleoside triphosphates. In addition, the results presented in the examples clearly show that these enzymes possess, on these substrates, an activity which is highly superior to the human enzyme. Thus, in the presence of 0.675 μg of human enzyme, the percentage of GCV triphosphate obtained is 1.5%, whereas in the presence of 0.75 μg of yeast enzyme, it is 82.9%. Likewise, in the presence of 6.75 μg of human enzyme, the percentage of GCV triphosphate obtained is 24%, whereas in the presence of 1.5 μg of yeast enzyme, it is 91.1% and in the presence of 5 μg of bovine enzyme, it is 92%. The same results are obtained with another nucleoside analogue, acyclovir. Thus, in the presence of 6.75 μg of human enzyme, the percentage of ACV triphosphate obtained is less than 0.4%, whereas in the presence of 1.5 μg of yeast enzyme, it is 8%, in the presence of 15 μg of yeast enzyme, it is 81% and in the presence of 5 μg of bovine enzyme, it is 1.3%. These results clearly demonstrate the advantage of using, in the combinations according to the invention, a yeast or bovine nucleoside diphosphate kinase. These results also show that the first step of phosphorylation of the analogue to the monophosphate is not necessarily the limiting step in the process and that the use of a combination of enzymes according to the invention makes it possible to increase the therapeutic potential of the treatment.

Moreover, the applicant has also shown that guanylate kinase from yeast, and especially from *Saccharomyces cerevisiae*, also made it possible to phosphorylate analogues of nucleoside monophosphates, such as ganciclovir monophosphate or acyclovir monophosphate, to nucleoside diphosphates with a good activity. Thus, in the presence of 2.5 μg of yeast enzyme, the percentage of GCV diphosphate obtained may exceed 92% and in the presence of 74 μg of yeast enzyme, the percentage of ACV diphosphate obtained is 54%. Furthermore, the results presented show that yeast guanylate kinase has a GCVMP phosphorylation rate which is twice as high as the human enzyme. Likewise, its affinity for GCVMP is greater than the affinity which the human enzyme exhibits for this substrate by a factor at least equal to 2. In total, the Vmax/Km value for the yeast enzyme for GCVMP is 4.4 times higher than the value exhibited by the human enzyme. For ACVMP, the Vmax/Km value for the yeast enzyme is 7 to 9 times higher than the value exhibited by the human enzyme for this substrate.

The applicant has also demonstrated that a coupling of these two nonhuman enzymes with thymidine kinase, for example the herpes virus type I thymidine kinase, made it possible to phosphorylate nucleoside analogues such as ganciclovir or acyclovir to triphosphate derivatives, with a very high efficiency.

According to a preferred embodiment, the compositions of the invention comprise sequences encoding guanylate kinase (EC-2.7.4.8) and/or nucleoside diphosphate kinase (EC-2.7.4.6) from yeast. More preferably, they are enzymes from the yeast *S. cerevisiae*. These sequences are used simultaneously with a sequence (HSV1-TK) encoding the herpes simplex virus type 1 thymidine kinase (EC-2.7.1.21) so as to make it possible to triphosphorylate the nucleoside analogues such as ganciclovir or acyclovir.

As indicated above, the compositions according to the invention may comprise a combination of enzymes or of nucleic acids allowing the in vivo production of the enzymes. They are advantageously nucleic acids. This embodiment is preferred since it allows an in vivo production of higher levels of enzymes as well as a greater therapeutic effect.

According to a first embodiment, in the compositions of the invention, the nucleic acids are carried by the same expression vector. This embodiment is particularly advantageous because only one vector has to be introduced into a mammalian cell for the desired therapeutic effect to be obtained. In this embodiment, the various nucleic acids may constitute three distinct expression cassettes inside the same expression vector. Thus, the various nucleic acids may each be placed under the control of a transcriptional promoter, of a transcriptional terminator and of distinct translation signals. It is also possible to insert several nucleic acids in the form of a polycistron whose expression is directed by a single promoter and a single transcriptional terminator. This may be performed especially by the use of IRES (Internal Ribosome Entry Site) sequences positioned between the nucleic sequences. In this regard, the expression vectors of the invention may comprise a bicistronic unit directing the expression of two nucleic acids, and optionally a separate nucleic acid encoding the third enzyme. The vectors of the invention may also comprise a tricistronic unit directing the expression of the three nucleic acids. These various embodiments are illustrated in the examples.

Preferred expression vectors for the purposes of the invention are especially:

A vector comprising:
   a first nucleic acid encoding a thymidine kinase, and,
   a second nucleic acid encoding a nonhuman guanylate kinase. It is preferably a yeast guanylate kinase.

A vector comprising:
   a first nucleic acid encoding a thymidine kinase, and,
   a second nucleic acid encoding a nucleoside diphosphate kinase. It is preferably a nonhuman eukaryotic nucleoside diphosphate kinase. More preferably, it is an NDPK of bovine or yeast origin.

Advantageously, this vector comprises, in addition, a nucleic acid encoding a guanylate kinase.

The thymidine kinase used in the vectors of the invention is advantageously a thymidine kinase of viral, especially herpetic, origin. It is preferably a thymidine kinase derived from the HSV-1 or HSV-2 virus TK.

As indicated above, in the vectors according to the invention, the various nucleic acids may be placed under the control of distinct promoters, or may constitute a polycistronic unit under the control of a single promoter. In this regard, as indicated above, the enzymes may also be produced in coupled form, the various nucleic acids being coupled in order to produce a protein carrying the various enzymatic activities. In particular, a specific embodiment of the vectors according to the invention is characterized in that the nucleic acid encoding the thymidine kinase of viral origin and the nucleic acid encoding nonhuman guanylate kinase are coupled and encode a protein carrying both the TK and GUK activities. According to another variant, in the vectors of the invention, the nucleic acid encoding the thymidine kinase of viral origin and the nucleic acid encoding the nucleoside diphosphate kinase are coupled and encode a protein carrying both the TK and NDPK activities. By way of illustration, the coupling between the enzymes is carried out by means of a peptide linker, for example of structure $(G_4S)_n$.

According to another embodiment, in the compositions of the invention, the nucleic acids are carried by several expression vectors.

As indicated below, the expression vectors may be of plasmid or viral origin. As regards vectors of viral origin, they are advantageously retroviruses or adenoviruses.

Various promoters may be used within the framework of the invention. They are sequences which allow the expression of a nucleic acid in a mammalian cell. The promoter is advantageously chosen from the promoters which are functional in human cells. More preferably, it is a promoter allowing the expression of a nucleic acid sequence in an hyperproliferative cell (cancer cell, restenosis, and the like). In this regard, various promoters may be used. This may be, for example, the actual promoter of the gene considered (TK, GMPK, NDPK). This may also be regions of different origin (responsible for the expression of other proteins, or even synthetic). This may thus be any promoter or derived sequence stimulating or repressing the transcription of a gene in a specific manner or otherwise, in an inducible manner or otherwise, in a strong or weak manner. There may be mentioned especially the promoter sequences of eukaryotic or viral genes. For example, they may be promoter sequences derived from the genome of the target cell. Among the eukaryotic promoters, there may be used in particular ubiquitous promoters (promoter of the HPRT, PGK, α-actin, tubulin and DHFR genes and the like), promoters of intermediate filaments (promoter of the GFAP, desmin, vimentin, neurofilament and keratin genes and the like), promoters of therapeutic genes (for example the promoter of the MDR, CFTR, Factor VIII and ApoAI genes and the like), tissue-specific promoters (promoter of the pyruvate kinase, villin, fatty acid binding intestinal protein and smooth muscle alpha-actin gene and the like), specific cell promoters of the dividing cell type, such as cancer cells or alternatively promoters corresponding to a stimulus (steroid hormone receptor, retinoic acid receptor, glucocorticoid receptor and the like) or labelled inducible. Likewise, they may be promoter sequences derived from the genome of a virus, such as for example the promoters of the adenovirus E1A and MLP genes, the CMV early promoter, or alternatively the RSV LTR promoter and the like. In addition, these promoter regions may be modified by addition of activating or regulatory sequences, or sequences allowing a tissue-specific or predominant expression.

Another subject of the invention relates to a product comprising a combination of enzymes capable of triphosphorylating a guanosine analogue, and the said guanosine analogue, for a simultaneous or separate administration or spread out over time.

The invention also relates to a composition for the in vivo production of a toxic nucleoside triphosphate analogue comprising, packaged separately or together:
   a nucleoside analogue
   a nucleic acid encoding a thymidine kinase
   a nucleic acid encoding a guanylate kinase, and,
   a nucleic acid encoding a nucleoside diphosphate kinase.

The subject of the invention is also a composition comprising a combination of enzymes involved in the phosphorylation of nucleosides, optionally generated in situ by expression of nucleic at least one of these enzymes being of nonhuman eukaryotic origin. The combination of enzymes comprises especially a TK and an NDPK; a TK and a GMPK or a TX, a GMPK and an NDPK.

The present invention also relates to a method for the destruction of proliferative cells, comprising the administration to the said cells of a combination of enzymes comprising a TK and an NDPK. Preferably, the combination comprises, in addition, a guanylate kinase. The invention also relates to a method for the destruction of proliferative cells, comprising the administration to the said cells of a combination of enzymes comprising a TK and a GMPK.

According to this method, the cells are brought into contact with a nucleoside analogue, preferably a guanosine analogue, which is converted in the cells expressing the combination of enzymes to a toxic compound.

According to the invention, enzymes may be administered to the cells by administration of nucleic acids encoding the said enzymes.

The invention also consists in the use of a nucleoside diphosphate kinase or of a nucleic acid encoding the latter, in combination with a thymidine kinase or a nucleic acid encoding a thymidine kinase, for the preparation of a pharmaceutical composition intended for the destruction of proliferative cells.

The invention also relates to a process for the triphosphorylation of a nucleoside analogue comprising the exposure of the said analogue to a combination of enzymes, at least one of them being of nonhuman eukaryotic origin.

The present invention now provides new therapeutic agents which make it possible to interfere with numerous cellular dysfunctions. With this objective in view, the nucleic acids or cassettes according to the invention may be injected as they are at the site to be treated, or incubated directly with the cells to be destroyed or treated. It has indeed been described that naked nucleic acids may penetrate into cells without a specific vector. However, the use of an administration vector, which makes it possible to improve (i) the efficiency of the cellular penetration, (ii) the cloning (iii) the extra- and intracellular stability, is preferred within the framework of the present invention. In a particularly preferred embodiment of the present invention, the nucleic sequences are incorporated into a transfer vector. The vector used may be of chemical, plasmid or viral origin.

Chemical vector is understood to cover, for the purposes of the invention, any nonviral agent capable of promoting the transfer and expression of nucleic sequences in eukaryotic cells. These chemical or biochemical, synthetic or naturally occurring vectors represent an advantageous alternative to the naturally occurring viruses, in particular for the sake of convenience, safety and also by the absence of a theoretical limit as regards the size of DNA to be transfected. These synthetic vectors have two principal functions, compact the nucleic acid to be transfected and promote its cellular attachment as well as its passage across the plasma membrane and, where appropriate, both nuclear membranes. To overcome the polyanionic nature of the nucleic acids, the nonviral vectors all possess polycationic charges. As a representative of this type of nonviral transfection techniques, currently developed for the introduction of genetic information, there may thus be mentioned those involving complexes of DNA and of DEAE-dextran (Pagano et al., J. Virol. 1 (1967)891), of DNA and of nuclear proteins (Kaneda et al., Science 243 (1989) 375), of DNA and of lipids (Felgner et al., PNAS 84 (1987) 7413), the use of liposomes (Fraley et al., J. Biol. Chem. 255 (1980) 10431), and the like.

The use of viruses as vectors for the transfer of genes appeared as a promising alternative to these physical transfection techniques. In this regard, various viruses were tested for their capacity to infect certain cellular populations. In particular, the retroviruses (RSV, EMS, MMS, and the like), the HSV virus, the adeno-associated viruses and the adenoviruses.

The nucleic acid or the vector used in the present invention may be formulated for topical, oral, parenteral, intranasal, intravenous, intramuscular, subcutaneous, intraocular, or transdermal administration, and the like. Preferably, the nucleic sequence or the vector is used in an injectable form. It may therefore be mixed with any pharmaceutically acceptable vehicle for an injectable formulation, especially a direct injection at the level of the site to be treated. They may be in particular isotonic sterile solutions or dry, especially freeze-dried, compositions which, upon addition depending on the case of sterilized water or of physiological saline, allow the constitution of injectable solutions. A direct injection of the nucleic acid sequence into the patient's tumour is advantageous because it makes it possible to concentrate the therapeutic effect at the level of the affected tissues. The doses of nucleic sequences used may be adapted according to various parameters, and especially according to the vector, the mode of administration used, the relevant pathology or the desired duration of treatment.

The invention also relates to any pharmaceutical composition comprising a combination of enzymes as defined above.

It also relates to any pharmaceutical composition comprising at least one vector as defined above.

It also relates to the use of an NDPK of yeast origin or a GMPK of yeast origin for the in vivo phosphorylation of nucleoside analogues.

Because of their antiproliferative properties, the pharmaceutical compositions according to the invention are most particularly suitable for the treatment of hyperproliferative disorders, such as especially cancers and restenosis. The present invention thus provides a particularly effective method for the destruction of cells, especially hyperproliferative cells. It is thus applicable to the destruction of tumour cells or of the smooth muscle cells of the vascular wall (restenosis). It is most particularly appropriate for the treatment of cancers. By way of example, there may be mentioned colon adenocarcinomas, thyroid cancers, lung carcinomas, myeloid leukaemias, colorectal cancers, breast cancers, lung cancers, gastric cancers, oesophageal cancers, B lymphomas, ovarian cancers, bladder cancers, glioblastomas, hepatocarcinomas, bone or skin cancers, cancers of the pancreas or cancers of the kidney and of the prostate, oesophageal cancers, cancers of the larynx, head and neck cancers, HPV-positive anogenital cancers, EBV-positive cancers of the nasopharynx and the like.

It may be used in vitro or ex vivo. Ex vivo, it consists essentially in incubating the cells in the presence of a nucleic sequence (or of a vector, or cassette or directly of the derivative). In vivo, it consists in administering to the organism an active quantity of a vector (or of a cassette) according to the invention, preferably directly at the level of the site to be treated (tumour in particular), prior to, simultaneously with and/or after the injection of the prodrug considered, that is to say ganciclovir or a nucleoside analogue. In this regard, the subject of the invention is also a method for the destruction of hyperproliferative cells which comprises bringing the said cells or part of them into contact with a combination of enzymes or of nucleic sequences as defined above, in the presence of a nucleoside analogue.

The present invention will be described more fully with the aid of the examples and figures below which should be considered to be illustrative and nonlimiting.

LEGEND TO THE FIGURES

FIG. 1: Schematic representation of the vector pCDNA3-TK

Figure 2:
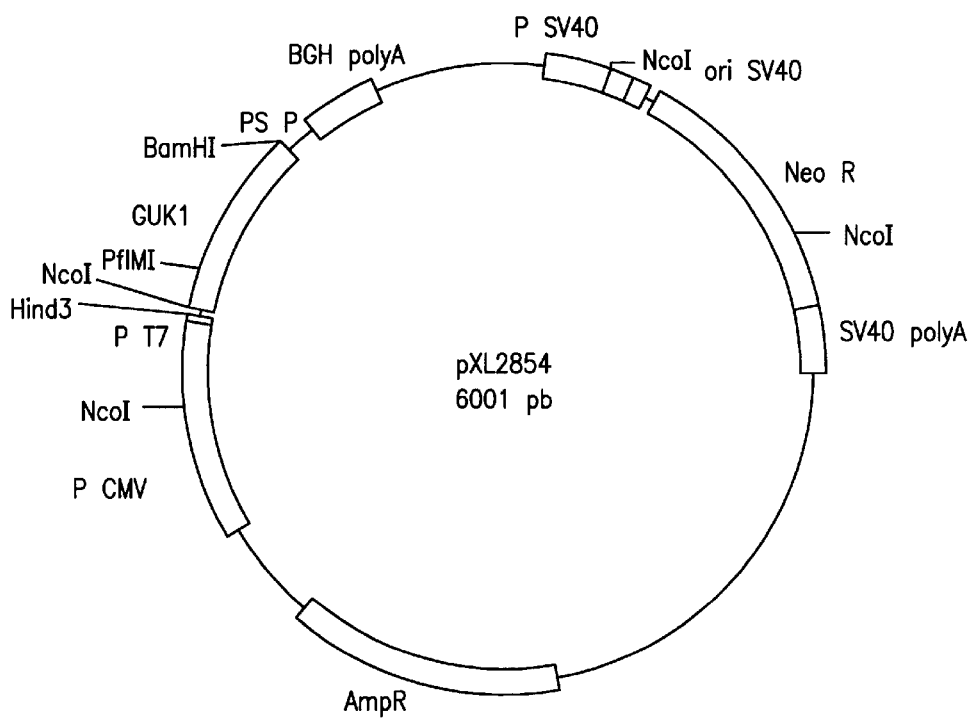

FIG. 2: Schematic representation of the vector pXL2854

Figure 3:
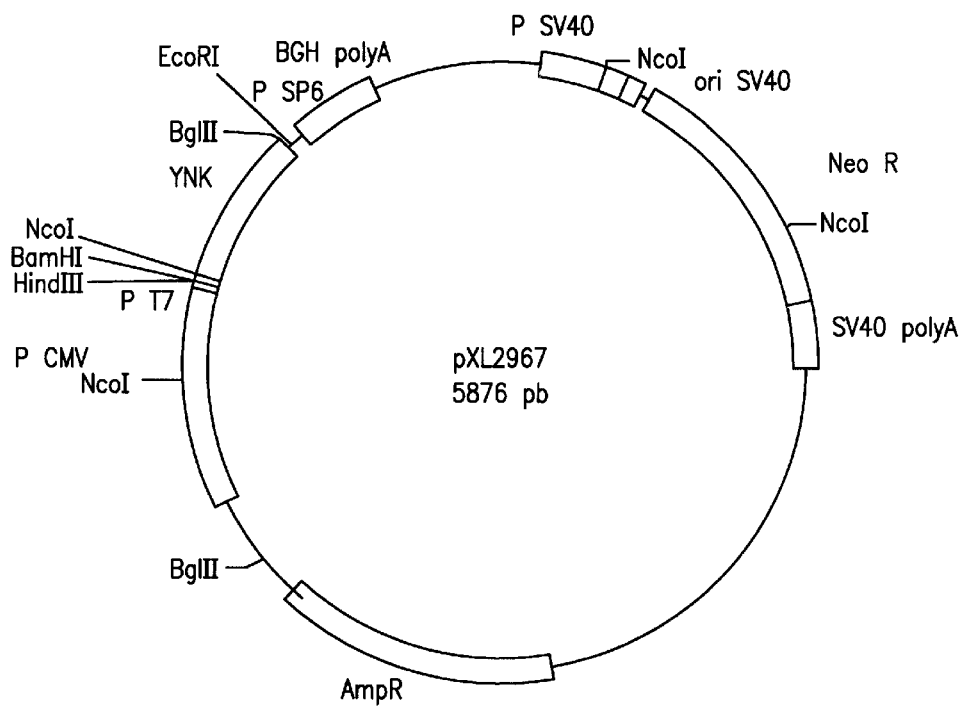

FIG. 3: Schematic representation of the vector pXL2967

Figure 4:
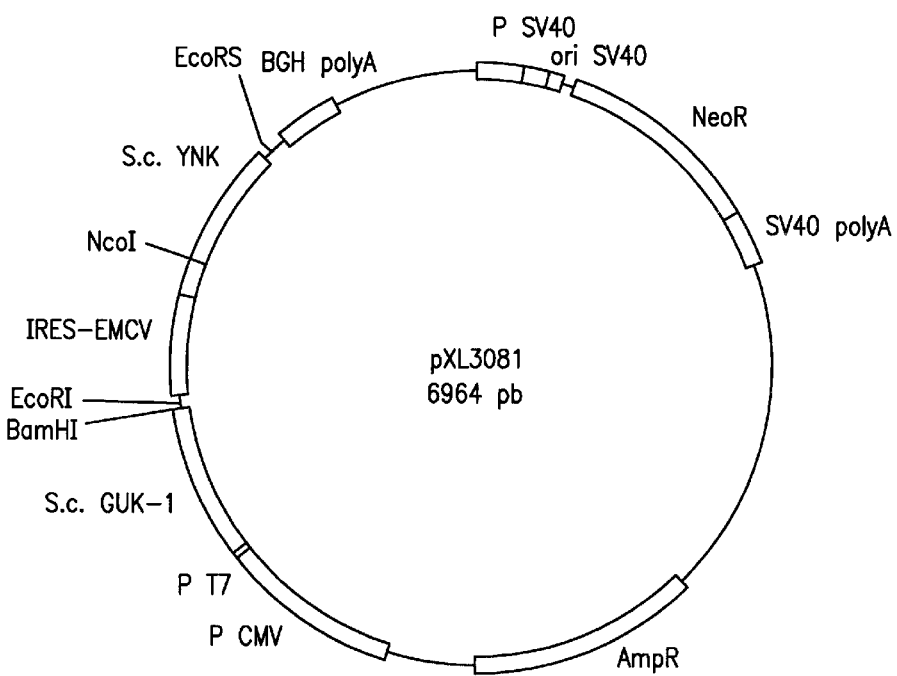

FIG. 4: Schematic representation of the vector pXL3081

Figure 5:
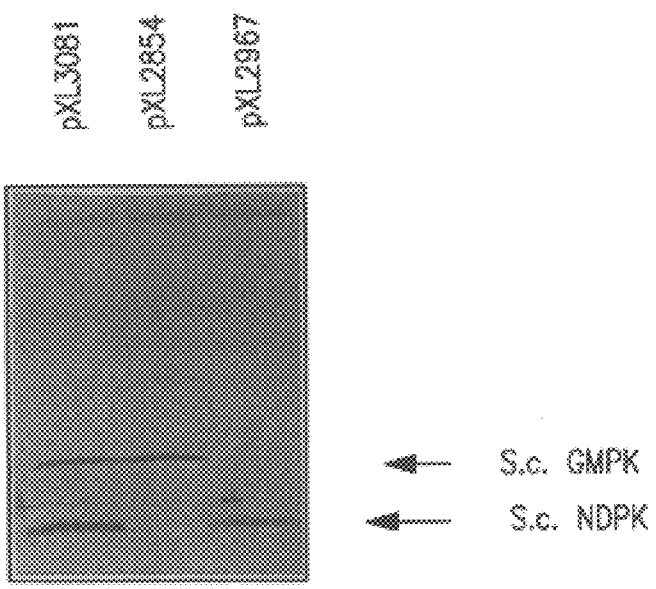

FIG. 5: Demonstration of the expression of the proteins GMPK and NDPK

Figure 6:
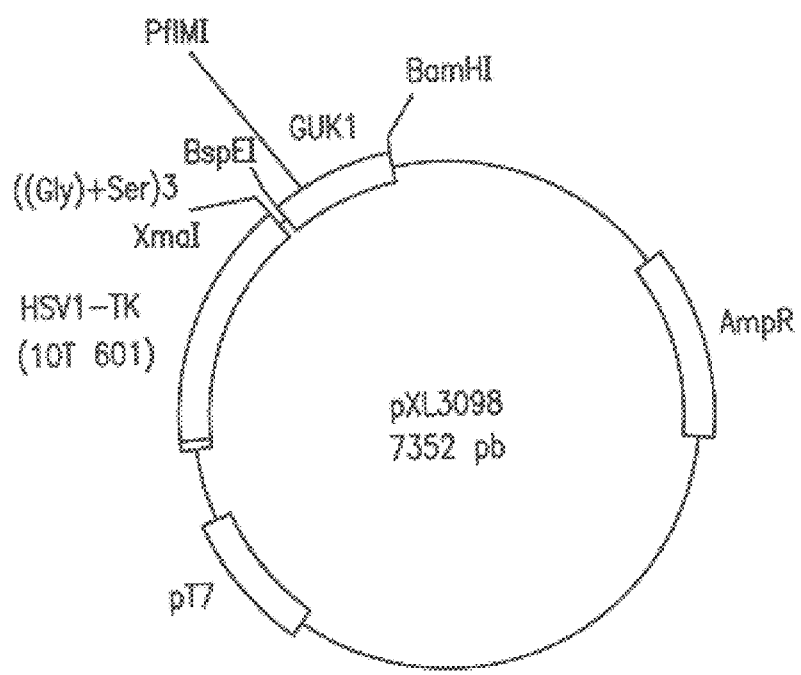

FIG. 6: Schematic representation of the vector pXL3098

Table 1: Kinetic constants for the yeast and human erythrocyte GMPKs on GCVMP and ACVMP. Published values: [D. F. Smée et al (1985) *Biochem. Pharmacol.* 34:1049–1056]$^a$; [R. E. Boehme (1984) *J. Biol. Chem.*

259:12346–12349][b]; [W. H. Miller and R. L. Miller (1980) *J. Biol. chem.* 255:7204–7207][c]

Table 2: TK-GMPK-NDPK coupling: % of products formed.

MATERIALS AND METHODS

ABBREVIATIONS

ACV: acyclovir
GCV: ganciclovir
GMPK: guanylate kinase
HSV1-TK: herpes simplex virus type 1 thymidine kinase
NDPK: nucleoside diphosphate kinase

General Molecular Biology Techniques

The methods conventionally used in molecular biology such as preparative extractions of plasmid DNA, centrifugation of plasmid DNA in a caesium chloride gradient, electrophoresis on agarose or acrylamide gels, purification of DNA fragments by electroelution, phenol-chloroform extraction of proteins, precipitation of DNA in saline medium with ethanol or isopropanol, and transformation in *Escherichia coli* are well known to persons skilled in the art and are abundantly described in the literature (Sambrook et al. "Molecular Cloning, a Laboratory Manual", Cold Spring Harbor Laboratory, Cold Spring Harbor, N.Y., 1989; Ausubel et al. "Current Protocols in Molecular Biology", John Wiley & Sons, New York, 1987).

The plasmids of the pUC type and the phages of the M13 series are of commercial origin (Bethesda Research Laboratories), the plasmids PBSK or pBKS are obtained from Stratagene.

The enzymatic amplification of DNA fragments by the so-called PCR technique [Polymerase-catalysed Chain Reaction] may be carried out using a DNA thermal cycler (Perkin Elmer Cetus) according to the recommendations of the manufacturer.

The electroporation of plasmid DNA into *E. coli* cells may be performed with the aid of an electroporator (Bio-Rad) according to the recommendations of the supplier.

The verification of the nucleotide sequences may be carried out by the method developed by Sanger et al. [Proc. Natl. Acad. Sci. USA, 74 (1977) 5463–5467] using the kit distributed by Amersham or that distributed by Applied Biosystems.

EXAMPLE 1

Construction of Vectors for Expression of the Combinations of Enzymes

This example describes various methods for the construction of vectors for expression and transfer of the nucleic sequences of the invention in vitro or in vivo.

1.1—Construction of Plasmid Vectors

For the construction of plasmid vectors, various types of expression vectors may be used. 2 types of vectors are more particularly preferred:

The vector pSV2, described in DNA Cloning, A practical approach Vol. 2, D. M. Glover (Ed) IRL Press, Oxford, Washington D.C., 1985. The vector is a eukaryotic expression vector. The nucleic acids encoding the combinations of enzymes of the invention may be inserted into this vector at the HpaI-EcoRV sites. They are thus placed under the control of the promoter of the SV40 virus enhancer.

The vector pCDNA3 (Invitrogen). It is also a eukaryotic expression vector. The nucleic sequences encoding the enzymes or combinations of enzymes of the invention are placed, in this vector, under the control of the early CMV promoter.

1.2—Construction of Viral Vectors

According to a specific embodiment, the invention consists in the construction and use of viral vectors allowing the in vivo transfer and expression of nucleic acids as defined above.

As regards more particularly adenoviruses, different serotypes, whose structure and properties vary somewhat, have been characterized. Among these serotypes, the use of type 2 or 5 human adenoviruses (Ad 2 or Ad 5) or adenoviruses of animal origin (see application WO 94/26914) is preferred in the context of the present invention. Among the adenoviruses of animal origin which can be used in the context of the present invention, there may be mentioned the adenoviruses of canine, bovine, murine, (example: Mav1, Beard et al., Virology 75 (1990) 81), ovine, porcine, avian or simian (example: SAV). Preferably, the adenovirus of animal origin is a canine adenovirus, more preferably a CAV2 adenovirus [Manhattan strain or A26/61 (ATCC VR-800) for example]. Preferably, adenoviruses of human or canine or mixed origin are used in the context of the invention.

Preferably, the defective adenoviruses of the invention comprise the ITRs, a sequence allowing the encapsidation and a nucleic acid according to the invention. Still more preferably, in the genome of the adenoviruses of the invention, at least the E1 region is nonfunctional. The viral gene considered may be made nonfunctional by any technique known to persons skilled in the art, and especially by total suppression, substitution, partial deletion, or addition of one or more bases in the gene(s) considered. Such modifications may be obtained in vitro (on the isolated DNA) or in situ, for example, by means of genetic engineering techniques, or alternatively by treatment by means of mutagenic agents. Other regions may also be modified, and especially the region E3 (WO 95/02697), E2 (WO 94/28938), E4 (WO 94/28152, WO 94/12649, WO 95/02697) and L5 (WO 95/02697). According to a preferred embodiment, the adenovirus according to the invention comprises a deletion in the E1 and E4 regions. According to another preferred embodiment, it comprises a deletion in the E1 region at the level of which the E4 region and the nucleic sequence of the invention are inserted (cf FR 94 13355). In the viruses of the invention, the deletion in the E1 region extends preferably from nucleotides 455 to 3329 on the sequence of the Ad5 adenovirus.

The defective recombinant adenoviruses according to the invention may be prepared by any technique known to persons skilled in the art (Levrero et al., Gene 101 (1991) 195, EP 185 573; Graham, EMBO J. 3 (1984) 2917). In particular, they may be prepared by homologous recombination between an adenovirus and a plasmid carrying, inter alia, a nucleic sequence or a combination of nucleic sequences of the invention. The homologous recombination occurs after co-transfection of the said adenoviruses and plasmid into an appropriate cell line. The cell line used should preferably (i) be transformable by the said elements, and (ii), comprise sequences capable of complementing the defective adenovirus genome part, preferably in integrated form in order to avoid risks of recombination. By way of example of a line, there may be mentioned the human embryonic kidney line 293 (Graham et al., J. Gen. Virol. 36 (1977) 59) which contains especially, integrated into its genome, the left-hand part of the genome of an Ad5 adenovirus (12%) or lines capable of complementing the E1 and E4 functions as described especially in applications Nos. WO 94/26914 and WO 95/02697 or in Yeh et al., J. Virol. 70 (1996) 559.

Next, the adenoviruses which have multiplied are recovered and purified according to conventional molecular biology techniques, as illustrated in the examples.

As regards the adeno-associated viruses (AAV), they are DNA viruses of a relatively small size, which integrate into the genome of the cells which they infect, in a stable and site-specific manner. They are capable of infecting a broad spectrum of cells, without inducing any effect on cell growth, morphology, or differentiation. Moreover, they do not appear to be involved in pathologies in man. The AAV genome has been cloned, sequenced and characterized. It comprises about 4700 bases, and contains, at each end, an inverted repeat region (ITR) of about 145 bases, serving as replication origin for the virus. The rest of the genome is divided into 2 essential regions carrying the encapsidation functions: the left-hand part of the genome, which contains the rep gene involved in the viral replication and the expression of the viral genes; the right-hand part of the genome, which contains the cap gene encoding the virus capsid proteins.

The use of AAV-derived vectors for the transfer of genes in vitro and in vivo has been described in the literature (see especially WO 91/18088; WO 93/09239; U.S. Pat. No. 4,797,368, U.S. Pat. No. 5,139,941, EP 488 528). These applications describe different AAV-derived constructs, in which the rep and/or cap genes are deleted and replaced by a gene of interest, and their use to transfer in vitro (on cells in culture) or in vivo (directly in an organism) the said gene of interest. The defective recombinant AAVs according to the invention may be prepared by co-transfection, into a cell line infected by a human helper virus (for example an adenovirus), of a plasmid containing a nucleic sequence or a combination of nucleic sequences of the invention bordered by two AAV inverted repeat regions (ITR), and of a plasmid carrying the AAV encapsidation genes (rep and cap genes). A usable cell line is for example the line 293. Other production systems are described for example in applications WO 95/14771; WO 95/13365; WO 95/13392 or WO 95/06743. The recombinant AAVs produced are then purified by conventional techniques.

As regards the herpes viruses and the retroviruses, the construction of recombinant vectors has been widely described in the literature; see especially Breakfield et al., New Biologist 3 (1991) 203; EP 453242, EP 178220, Bernstein et al. Genet. Eng. 7 (1985) 235; McCormick, BioTechnology 3 (1985) 689, and the like. In particular, the retroviruses are integrative viruses, selectively infecting dividing cells. They therefore constitute vectors of interest for cancer applications. The genome of the retroviruses comprises essentially two LTRs, an encapsidation sequence and three coding regions (gag, pol and env). In the recombinant vectors derived from the retroviruses, the gag, pol and env genes are generally deleted, completely or in part, and replaced by a heterologous nucleic acid sequence of interest. These vectors may be prepared from different types of retroviruses such as especially MoMuLV ("murine Moloney leukaemia virus"; also called MOMLV), MSV ("murine Moloney sarcoma virus"), HaSV ("Harvey sarcoma virus"); SNV ("spleen necrosis virus"); RSV ("Rous sarcoma virus") or Friend's virus.

To construct the recombinant retroviruses according to the invention comprising a nucleic nucleic sequence or a combination of nucleic sequences according to the invention, a plasmid comprising especially the LTRs, the encapsidation sequence and the said nucleic sequence is constructed, and then used to transfect a so-called encapsidation cell line, capable of providing in trans the retroviral functions deficient in the plasmid. Generally, the encapsidation lines are therefore capable of expressing the gag, pol and env genes. Such encapsidation lines have been described in the prior art, and especially the line PA317 (U.S. Pat. No. 4,861,719); the line PsiCRIP (WO 90/02806) and the line GP+envAm-12 (WO 89/07150). Moreover, the recombinant retroviruses may comprise modifications at the level of the LTRs in order to suppress the transcriptional activity, as well as extended encapsidation sequences, comprising part of the gag gene (Bender et al., J. Virol. 61 (1987) 1639). The recombinant retroviruses produced are then purified by onventional techniques.

To carry out the present invention, it is most particularly advantageous to use an adenovirus or a defective recombinant retrovirus. These vectors indeed possess particularly advantageous properties for the transfer of suicide genes into tumour cells.

1.3—Chemical Vectors

The nucleic acids or the vectors for plasmid expression which are described in this example (1.1) and in Example 2 may be administered as they are in vitro or ex vivo. It has indeed been shown that naked nucleic acids could transfect cells. However, to improve the transfer efficiency, the use of a transfer vector is preferred within the framework of the invention. It may be a viral vector (Example 1.2. ) or a synthetic transfection agent.

Among the synthetic vectors developed, the use of the cationic polymers of the following types: polylysine, (LKLK)(SEQ ID NO:10)n, (LKKL)(SEQ ID NO:11)n, (PCT/FR/00098) polyethylene imine (WO 96/02655) and DEAE dextran, or alternatively the cationic lipids or lipofectants is preferred within the framework of the invention. They possess the property of condensing the DNA and of promoting its association with the cell membrane. Among these, there may be mentioned the lipopolyamines (lipofectamine, transfectam, and the like), different cationic or neutral lipids (DOTMA, DOGS, DOPE and the like) as well as peptides of nuclear origin. In addition, the concept of targeted transfection was developed, mediated by a receptor, which takes advantage of the principle of condensing the DNA by virtue of the cationic polymer while directing the attachment of the complex to the membrane by virtue of a chemical coupling between the cationic polymer and the ligand of a membrane receptor, which is present at the surface of the cell type which it is desired to grasp. The targeting of the transferrin and the insulin receptors or of the receptor for the asialoglycoproteins of the hepatocytes has thus been described. The preparation of a composition according to the invention using such a chemical vector is performed according to any technique known to persons skilled in the art, generally by simply placing the various components in contact.

EXAMPLE 2

Cloning of HSV1-TK and/or of Guanylate Kinase and/or of Nucleoside Diphosphokinase in a Eukaryotic Expression Vector This example describes a specific embodiment of the invention, using a plasmid expression vector system to produce in situ the combinations of enzymes of the invention.

The expression of prokaryotic or eukaryotic genes in mammalian cells is known to persons skilled in the art. To optimize this expression, the vectors of the invention described below comprise the following signals: i) a promoter/enhancer such as the CMV promoter which is well expressed in human cells; ii) a Kozak sequence whose consensus is (G/A)NNAUG(G/A); iii) the gene to be expressed; followed iv) by a polyadenylation sequence (V. Chisholm 1995 DNA cloning Vol. 4, ed. D. Glover and B. Hames p1). Such constructions are possible with the aid of commercial vectors such as the vectors pZeoSV, pcDNA3 and the like, and were performed with the genes encoding HSV1-TK, GMPK and NDK from *S. cerevisiae*.

2.1—Vector for Expression of ESV1-TK

The HSV1-TK gene encoding the herpes simplex virus type 1 thymidine kinase, derived from the plasmid pHSV-106 (Gibco-BRL) was cloned into the eukaryotic expression vector pcDNA3 (Invitrogen). This plasmid pcDNA3-TK of 6936 bp was constructed by introducing the 1.5 kb EcoRI-NotI insert obtained from pBTK1 between the EcoRI and NotI sites of pcDNA3, see FIG. 1. The plasmid pBTK1 was obtained in the following manner: After having made the ends blunt, the 1.5 kb BglII-NcoI insert obtained from pHSV-106 and containing the HSV1-TK gene, whose sequence is published by McKnight 1980 Nucl. Acids Res. 8 p5931, was cloned into the SmaI site of pBSK.

The insert of the plasmid pcDNA3-TK contains i) 60 bp upstream of the HSV1-TK gene comprising the Kozak sequence (CGTATGG), ii) the gene sequence (1.13 kb) which is identical to that published by McKnight 1980 Nucl. Acids Res. 8 p5931, iii) the 3' sequence of the gene (0.3 kb) which is also described by McKnight.

2.2—Vector for Expression of Guanylate Kinase

The 561 bp GUK1 gene encoding *S. cerevisiae* guanylate kinase derived from pGUK-1 (see Example 3), was cloned into the eukaryotic expression vector pcDNA3 (Invitrogen) after having introduced a Kozak consensus. This plasmid pXL2854 was obtained in the following manner. The XbaI-BamHI insert of pGUK-1 containing the GUk1 gene was cloned into the plasmid pSL301 (Invitrogen) between the XbaI-BamHI sites such that the GUK1 gene may then be excised by the HindIII and BamHI enzymes and be cloned between the HindIII and BamHI sites of pcDNA3 to generate a plasmid pcDNA3-GUK1.

Between the HindIII and PflMI sites of this plasmid is cloned a 150 bp HindIII-PflMI fragment containing a Kozak consensus and the 5' region of GUK1 to form the 6001 bp plasmid pXL2854, see FIG. 2. The 150 bp HindIII-PflMI fragment was isolated from a 280 bp fragment amplified by PCR with the aid of the plasmid pGUK-1 and sense oligonucleotide 6915 5' (GAG AAG CTT GCC ATG GCC CGT CCT ATC GTA A)3' (SEQ ID No. 1) and antisense oligonucleotide 6916 5' (GAG GAT CCG TTT GAC GGA AGC GAC AGT A)3' (SEQ ID No. 2), the hybridization taking place at 45° C. (the Kozak consensus being underlined in the oligonucleotide 6915). The nucleic sequence amplified by PCR was sequenced and exhibits two differences compared with the published sequence (M. Konrad 1992 J. Biol. Chem. 267 p25652) corresponding to the changes S2A (Serine at position 2 replaced by an alanine) and V34A (Valine at position 34 replaced by an alanine).

2.3—Vector for Expression of Nucleoside Diphosphokinase

The YNK gene encoding the *S. cerevisiae* nucleoside diphosphokinase, derived from the plasmid pAD1-YNK (K. Watanabe et al. 1993 Gene 29 p141), was cloned into the eukaryotic expression vector pcDNA3 (Invitrogen) after having introduced a Kozak consensus. This plasmid pXL2967 was obtained in the following manner. A PCR amplification was carried out with the plasmid pAD1-YNK as template and the sense oligonucleotide 7017 5= (AAG GAT <u>CCA CCA TGG</u> CTA GTC AAA CAG AAA)3' (SEQ ID No. 3) and the antisense oligonucleotide 7038 5' (AAG AAT TCA GAT CTT CAT TCA TAA ATC CA)3' (SEQ ID No. 4) at the hybridization temperature of 40° C. (the Kozak consensus being underlined in the oligonucleotide 7017). The 477 bp amplified fragment is digested with BamHI and EcoRI and then cloned between the BamHI and EcoRI sites of pcDNA3 to generate the 5861 bp plasmid pXL2967, see FIG. 3. The sequence of the PCR-amplified fragment is the same as that published for the YNK gene except at position 4 which corresponds to a change S2A S2A (Serine at position 2 replaced by an alanine) for the NDPK protein (K. Watanabe et al. 1993 Gene 29 p141).

2.4—Vector for the Co-expression of 2 Genes

The co-expression of genes may be performed in several ways known to persons skilled in the art. A preferred embodiment consists in introducing, between the sequences to be expressed, internal ribosome entry sites, IRES sequences (Mountford et al., TIG 11 (1995) 179).

An IRES sequence and the YNK gene are introduced in 3' of the cloned GUK1 gene into pcDNA3 to generate a vector allowing the co-expression of GUK1 and YNK, in the form of a bicistronic unit (vector pGUK1-YNK). More precisely, the IRES (internal ribosome entry site) sequence of the EMCV (encephalomyocartis virus) obtained from the plasmid pCITE (Novagen) was recloned by PCR between the EcoRI and NcoI sites and introduced at the EcoRI and EcoRV sites of the plasmid pBluescript (Stratagene) to generate the plasmid pXL3065. The 477 bp NcoI-EcoRV fragment containing the YNK gene derived from the plasmid pXL2967 is cloned between the NcoI and EcoRV sites of pXL3065 to form the plasmid pXL3079. The 1 kb BamHI-EcoRV fragment containing the IRES and the YNK gene of the plasmid pXL3079 is then cloned between the BamHI and EcoRV sites of the plasmid pXL2854 to generate the plasmid pXL3081. This plasmid contains the CMV and T7 promoters upstream of the GUK1 gene encoding *S. cerevisiae* guanylate kinase itself followed by the IRES and the YNK gene encoding *S. cerevisiae* nucleoside diphosphokinase, see FIG. 4. The expression of the GMPK and NDPK proteins was tested with the aid of the plasmids pXL2854, pXL2967 and pXL3081 in a reticulocyte transcription/translation system obtained from Promega, see FIG. 5. The results obtained show that the GMPK and NDPK proteins are co-expressed with the plasmid pXL3081.

The same approach is used to generate a vector co-expressing TK and YNK (vector pTK-YNK), or TK and GUK1 (vector pTK-GUK1).

2.5—Vector for the Co-expression of 3 Genes

The sequence encoding TK is inserted into the vector pGUK1-YNK of Example 2.4 above to generate a vector capable of expressing the 3 enzymatic activities (vector pTK-GUK1-YNK).

2.6—Vector for the Expression of an HSV1-TK/*S. cerevisiae* GMPK Fusion

The construction of fusion protein is well known to a person skilled in the art and is performed by the creation of a peptide linker between the C-terminal part of a protein and the N-terminal part of the other protein (1989 Nature 339 p394). Such a protein allows the cellular co-localization of enzymes and may also promote the "tunnelling" of substrate (Ljungcrantz et al. 1989 Biochemistry 28 p8786).

A fusion protein was produced by linking, with the aid of the linker —(Gly)4-Ser-(Gly)4-Ser-(Gly)4 (SEQ ID No. 9) the C-terminal sequence of HSV1-TK (Asn376) and the

19

N-terminal sequence of GMPK from *S. cerevisiae* (Ser2). The plasmid pXL3098, allowing the production of this fusion protein, was constructed in the following manner. The 3' sequence of the HSV1-TK gene (positions 1108 to 1128) was cloned by hybridization of the sense oligonucleotide 5' (CCG GGA GAT GGG GGA GGC TAA CGG AGG TGG CGG TTC TGG TGG CGG AGG CTC CG)3' (SEQ ID No. 5) and antisense oligonucleotide 5' (GAT CCG GAG CCT CCG CCA CCA GAA CCG CCA CCT CCG TTA GCC TCC CCC ATC TC)3' (SEQ ID No. 6), such that the Asn codon of the HSV1-TK gene (position 1128 bp) is followed by codons encoding the amino acids ((Gly)$_4$Ser)$_2$Gly. The 58 bp fragment is thus cloned between the XmaI and BamHI sites of pNEB193 (Biolabs) to generate the plasmid PTKL+. The 5' sequence of the *S. cerevisiae* GUK1 gene is amplified by PCR with the aid of the template pXL2854 and the sense oligonucleotide 5' (GAG AAT TCC GGA GGC GGT GGC TCC CGT CCT ATC GTA)3' (SEQ ID No. 7) and the antisense oligonucleotide 5' (GAG GAT CCG TTT GAC GGA AGC GAC AGT A)3' (SEQ ID No. 8), such that the Ser codon at position 2 of GMPK is preceded by (Gly)3Ser codons. This 0.27 kb fragment is cloned between the BamHI and EcoRI sites of pUC19 (Biolabs) to form a plasmid which is then cut with PflMI and BamHI in order to introduce therein the 0.44 kb PflMI-BamHI fragment of pXL2854 containing the 3' sequence of GUK1, and to generate the plasmid PGUKL-. The 0.58 kb BspEI-XbaI fragment of pGUKL- is inserted between the BspEI and XbaI sites of pTKL+ to create pTKLGUK. The 0.63 kb XmaI-BamHI insert of pTKLGUK is then cloned between the XmaI and BamHI sites of the expression vector pET11a, to form the plasmid pXL3098, see FIG. 6. This plasmid is then introduced into the strain BL21DE3met- and leads to the production of the protein TK-((Gly)$_4$Ser)$_3$-GMPK.

The fusion protein is then purified to homogeneity and the kinetic parameters of phosphorylation of the GCV and the ACV of this enzyme are compared with the kinetic parameters obtained with the proteins HSV1-TK and GMPK from *S. cerevisiae*.

2.7—Transfer and Expression in Vivo

The vectors described in Examples 2.1 to 2.6 are used for the in vivo transfer and expression of combinations of enzymes according to the invention. With this aim in view, various compositions comprising the said vectors are prepared:

- a composition comprising the vector pcDNA3-TK, the vector pXL2854 and lipofectamine,
- a composition comprising the vector pcDNA3-TK, the vector pXL2967 and lipofectamine.
- a composition comprising the vector pcDNA3-TK, the vector pXL2854, the vector pXL2967 and lipofectamine
- a composition comprising the vector pTK-GUK1 and lipofectamine, optionally in combination with the vector pXL2967,
- a composition comprising the vector pTK-YNK and lipofectamine, optionally in combination with the vector pXL2854, and
- a composition comprising the vector pTK-GUK1-YNK and lipofectamine The lipofectamine may be replaced by another chemical vector as described in Example 1.3.

20

These various compositions are used in vivo or ex vivo for the intracellular transfer and expression of combinations of enzymes according to the invention. They may also be used on cell cultures, and for example on fibroblast cell cultures NIH3T3 or human colon carcinoma cells HCT116. After transfer of the vectors, the nucleoside analogue is administered and the cellular destruction is demonstrated.

EXAMPLE 3

Purification of the Guanylate Kinase

Acellular extracts of *E. coli* strains overexpressing *S. cerevisiae* GMPK may be prepared in various ways, among which there may be mentioned lysis with lysozyme in the presence of EDTA, the use of grinding apparatus of the Menton-Golin, French Press or X-Press types, or the action of ultrasound. More particularly, the acellular extracts of *E. coli* strains overexpressing *S. cerevisiae* GMPK were prepared in the following manner:

The *E. coli* strain BL21 (DE3) pGUK-1 is cultured as described by M. Konrad in J. Biol. Chem. 267 p25652 in 1992. After centrifugation (5000×g; 20 min.), the cells obtained from 1 l of culture are resuspended in 20 ml of 20 mM Tris/HCl buffer pH 7.5, containing 1 mM EDTA and sonicated for 4 min at 4° C. After centrifugation (50,000×g; 1 h), the supernatant is injected onto a MONO Q HR 10/10 column (Pharmacia) equilibrated in 20 mM Tris/HCl buffer pH 7.5. The proteins are eluted with a linear gradient of 0 to 500 mM NaCl in 20 mM Tris/HCl buffer pH 7.5. The fractions containing the GMPK activity are combined and concentrated, and then chromatographed on a Superdex 75 HR16/10 column (Pharmacia) diluted with 50 mM Tris/HCl buffer pH 7.5, 150 mM NaCl. The fractions containing the GUK activity are combined. After this stage, the preparation has a single visible band in SDS-PAGE, after staining with Coomassie blue, and this band migrates with an apparent molecular weight of about 21,000.

The GMPK activity is conventionally assayed using an assay procedure described in the literature, Agarwal et al. 1978 Meth. Enzymol. vol. LI p483.

EXAMPLE 4

Determination of the Kinetic Constants for *S. cerevisiae* Guanylate Kinase.

The kinetic constants for the yeast GMP kinase purified as described in Example 3 are determined under the following enzymatic assay conditions:

The yeast GMP kinase is incubated for 10 min at 30° C. in 100 µl of 50 mM Tris/HCl buffer pH 7.8 containing 4 mM ATP, 10 mM MgCl$_2$, 100 mM KCl, 1 mg/ml BSA (bovine serum albumin) and 5–100 µM [8-3H]GCVMP (40 nCi/nmol) or 200–3200 µM [8-3H]ACVMP (40 nCi/nmol). he reaction is stopped by heating the reaction mixture for 3 min at 80° C., 50 µl of 10 mM potassium phosphate buffer pH 3.5 are added, and after centrifugation for 2 min at 10,000×g, 100 µl of supernatant are analysed by high performance liquid chromatography (HPLC) in the following system:

Stationary phase:
  Partisphere SAX (WHATMAN)—particle diameter: 5 µm
  Dimensions: 4.6×125 mm.
Mobile Phase:
  Buffer A: 0.01 M KH$_2$PO$_4$, pH 3.5 (adjusted with the aid of concentrated H$_3$PO$_4$)
  Buffer B: 0.75 M KH$_2$PO$_4$, pH 3.5 (adjusted with the aid of concentrated H$_3$PO$_4$)

Flow rate:
  1 ml/min
Gradient:

| Minute | % A | % B |
|---|---|---|
| 0 | 100 | 0 |
| 5 | 100 | 0 |
| 30 | 0 | 100 |
| 40 | 0 | 100 |
| 42 | 100 | 0 |
| 45 | 100 | 0 |

Detection:
  UV: 265 nm
  Radiochemical: tritium detection flow rate of the scintillant (Berthold's Optisafe 1) 1 ml/min for the calculation of the kinetic constants, the quantity of yeast GMP kinase introduced into the enzymatic reaction is adjusted so as to convert at most 10% of the substrate initially introduced. The Michaelis curves are adjusted to the experimental points with the aid of the Grafit software (Sigma). The results are presented in Table 1. They show that the yeast GMP kinase is capable of phosphorylating the GCVMP and ACVMP. Furthermore it exhibits a GCVMP phosphorylation rate twice as high as the human enzyme. Likewise, its affinity for GCVMP is greater than the affinity of the human enzyme for this substrate by a factor equal to at least 2. In total, the Vmax/Km value for the yeast enzyme for GCVMP is 4.4 times higher than the value exhibited by the human enzyme. For substrates entering into competition, the Vmax/Km constant determines the specificity of the enzyme for these substrates. It is known by the name of "specificity constant" [A. Fersht, Enzyme Structure and Mechanism, 1985, W. H. Fréeman and Co., London].

In the same manner, the yeast GMP kinase has an ACVMP phosphorylating capacity which is substantially greater than the human enzyme. The Vmax/Km value of the yeast enzyme for ACVMP is 7 to 9 times higher than the value which the human enzyme exhibits for this substrate.

EXAMPLE 5

Coupling of the TK, GMPK and NDK Enzymatic Activities:

In a preferred coupling mode, the incubation is carried out in 100 μl of 50 mM Tris/HCl buffer pH 7.8, containing 1 mg/ml of BSA (bovine serum albumin), 5 mM ATP, 4 mM MgCl$_2$, 12 mM KCl, 2 mM DTT, 600 μM EDTA, 100 μM [8-3H]-GCV (40 nCi/nmol) or 100 μM [2-3H]-ACV 40 nCi/nmol and various quantities of TK, GuK and NDPK (cf Table 2). The NDPKs of 3 organisms were used (enzymes marketed by SIGMA), as indicated in Table 2.

The coupling of the enzymes HSV1-TK and GMPK from S. cerevisiae allows a 90% phosphorylation of ganciclovir to ganciclovir diphosphate. The nucleoside diphosphokinase from baker's yeast, that is to say from S. cerevisiae, coupled to the enzymes HSV1-TK and GMPK, allows phosphorylation to ganciclovir triphosphate with a better activity than what is allowed by the human nucleoside diphosphokinase from erythrocytes. Comparable results are obtained with acyclovir. These results clearly demonstrate (a) that the combination of enzymes according to the invention provides a significant improvement in the phosphorylation, indicating that the sole modification of TK could not suffice to improve the properties of the system, (b) that the system of the invention makes it possible to increase the efficacy of treatment by the TK suicide gene, (c) that some non-human enzymes possess a better activity for the nucleoside analogues, making their use particularly advantageous.

EXAMPLE 6

Purification of the HSV1-TK/S. cerevisiae GMPK Fusion Protein

Acellular extracts of E. coli strains overexpressing the fusion protein may be prepared in various ways, among which there may be mentioned lysis with lysozyme in the presence of EDTA, the use of Menton-Golin-type grinding apparatus, French Press, X-Press or the action of ultrasound. More particularly, the acellular extracts of E. coli strains overexpressing the fusion protein were prepared in the following manner:

The E. coli strain BL21 DE3 pXL3098 is cultured in LB medium. After centrifugation (5000×g; 20 min), the cells obtained from 1 l of culture are resuspended in 20 ml of buffer A: 50 mM Tris/HCl pH 7.8, containing 5 mM DTT, 4 MM MgCl$_2$, 10% (v/v) Glycerol, 2 mM Benzamidine, 50 μl/l E64 (solution containing 100 μg/l N-[N-(L-3-trans-carboxyoxiran-2-carbonyl)-L-leucyl]-4-aminobutylguanidine, 0.2 mM Pefabloc, STI (Soybean trypsin inhibitor), 2 mg/ml Leupeptin, and sonicated for 4 min at 4° C. After centrifugation (50,000×g; 1 h), the supernatant is injected onto a MONO Q HR 10/10 column (Pharmacia) equilibrated in buffer A. The proteins are eluted with a 0 to 400 mM NaCl linear gradient in 20 mM Tris/HCl buffer pH 7.5. The fractions containing the TK and GMPK activity are grouped together and concentrated and then, chromatographed on a Superdex 200 HILoad 26/60 column (Pharmacia) eluted with buffer A containing 150 mM NaCl. The fractions containing the TK and GMPK activity are grouped together. At this stage, the preparation has a single band visible in SDS-PAGE, after staining with Coomassie blue, and this band migrates with an apparent molecular weight of about 61,000.

EXAMPLE 7

Study of Phosphorylation by the HSV1-TK/GMPK Fusion

This example describes a study of the kinetic parameters of phosphorylation of GCV and ACV of the fusion, compared with the kinetic parameters obtained with the proteins HSV1-TK and GMPK from S. cerevisiae. 7.1. Assay of the TK activity The activity of TK is assayed as follows: an enzymatic extract containing about 0.1 unit of TK is incubated for 15 min at 37° C. in 100 μl of 50 mm Tris/HCl buffer pH 7.8 containing 1 mg/ml of BSA (bovine serum albumin), 5 mM ATP, 4 mM MgCl$_2$, 12 mM Kcl, 2 mM DTT, 600 μM EDTA and 100 μM GCV+[8-3H]-GCV 40 nCi/nmol. The reaction is stopped by the addition of 10 μl of 50 mM Tris/HCl buffer pH 7.8 containing 1 mM nonradioactive thymidine. The phosphorylated species are attached onto a DEAE sephadex column (400 μl of gel) and then, after washing the column, these species are eluted with 2 ml of 1 M HCl. The radioactivity in the sample is then counted by liquid scintillation.

7.2. Assay of the GMPK Activity

The activity of GMPK is conventionally assayed using an assay protocol described in the literature, K. C. Agarwal et al. (Methods in Enzymology (1978) Vol. LI 483–490).

7.3. Assay of the Activity of the Fusion Protein and of the Coincubation of the TK and GMPK Enzymes The capacity of the TK-GMPK fusion protein to convert GCV or ACV to GCVDP or ACVDP compared with a synthetic mixture of TK and GMPK is determined in the following manner:

The incubation takes place in 200 μl of 50 mM Tris/HCl buffer pH 7.8 containing 1 mg/ml of BSA (bovine serum albumin), 5 mM ATP, 4 mM $MgCl_2$, 12 mM KCl, 2 mM DTT, 600 μM EDTA, 1 to 100 μM GCV+[8-3H]GCV (40 nCi/nmol) or 1 to 100 μM ACV+[2-3H]ACV 40 nCi/nmol and various quantities of TK, GMPK and the equivalent quantities of fusion protein. The reaction is stopped by heating for 3 min at 80° C.; after centrifugation, 100 μl of incubation product are analyzed in the following system:

Stationary phase:
Partisphere SAX (WHATMAN)—particle diameter: 5 μm.
Dimensions: 4.6×125 mm.

Mobile Phase:
Buffer A: 0.01 M $KH_2PO_4$ pH 3.5 (adjusted with the aid of concentrated $H_3PO_4$)
Buffer B: 0.75 M $KH_2PO_4$ pH 3.5 (adjusted with the aid of concentrated $H_3PO_4$)

Flow Rate:
1 ml/min

Gradient:

| Minute | % A | % B |
|---|---|---|
| 0 | 100 | 0 |
| 5 | 100 | 0 |
| 30 | 0 | 100 |
| 40 | 0 | 100 |
| 42 | 100 | 0 |
| 45 | 100 | 0 |

Detection:
UV: 265 nm
Radiochemistry: detection of tritium flow rate of the scintillant (Berthold's Optisafe 1) 1 ml/min The coupling and the combination of the enzymes HSV1-TK and GMPK from *S. cerevisiae* allow the phosphorylation of ganciclovir to ganciclovir diphosphate (see Table 3). Comparable results are obtained with acyclovir (see Table 3).

These results clearly show that the TK-GMPK fusion protein retains the properties of the original two enzymes. Furthermore, according to the operating conditions, the TK-GMPK fusion protein provides significant improvement in phosphorylation a) ranging up to a factor of 1.8 for GCV b) ranging up to a factor of 1.2 for ACV compared with the coincubation of the wild-type TK enzyme and the GMPK enzyme.

The fusion protein allows in vivo colocalization of the enzymatic activities in the cell, the separated enzymes being distributed in the nucleus for HSV1-TK and in the cytosol for GMPK. This construct therefore makes it possible to increase the efficiency of treatments by a suicide gene.

These results as a whole clearly demonstrate the therapeutic value of the present invention, making it possible both to reduce the doses of nucleoside and of enzymes and to obtain a substantial pharmacological benefit.

TABLE 1

KINETIC CONSTANTS OF GUANYLATE KINASES FROM YEAST AND FROM HUMAN ERYTHROCYTES FOR GCVMP and ACVMP

| | | Yeast guanylate kinase (*S. cerevisiae*) | | | Human guanylate kinase (erythrocytes) | | |
|---|---|---|---|---|---|---|---|
| Substrate | Km (μM) | Vmax (μmol/min/mg) | Vmax/Km | Km (μM) | Vmax (μmol/min/mg) | Vmax/Km |
| GCVMP | 18 | 40 | 2.2 | 40[a]<br>42–54[b] | 20[a] | 0.5[a] |
| ACVMP | 280 | 22 | 0.08 | 218[a]<br>209–753[b]<br>330[c] | 1.9[a]<br><br>3.6[c] | 0.009[a]<br><br>0.011[c] |

TABLE 2

TK-GMPK-NDPK COUPLING: % PER NI OF THE PRODUCTS FORMED

| | | | | NDPK | | | | | |
|---|---|---|---|---|---|---|---|---|---|
| SUBSTRATE | TK Qty | GMPK Qty | BAKER'S YEAST Qty | HUMAN (erythrocyte) | BOVINE (liver) Qty | % per NI OF THE PRODUCTS FORMED | | | INCUBATION TIME |
| 100 μm | (μg) | (μg) | (μg) | Qty (μg) | (μg) | N | NMP | NDP | NTP | min |
| GCV | 10.4 | 7.4 | | | | 3.9 | 5.3 | 90.8 | | 30 |
| | 2.6 | 2.5 | | | | 3.5 | 7.5 | 89.0 | | 30 |
| | 1.3 | 2.5 | | | | 2.9 | 4.4 | 92.7 | | 60 |
| | 10.4 | 7.4 | 1.5 | | | 1.1 | 0.9 | 6.9 | 91.1 | 30 |

TABLE 2-continued

TK-GMPK-NDPK COUPLING: % PER NI OF THE PRODUCTS FORMED

| SUBSTRATE 100 µm | TK Qty (µg) | GMPK Qty (µg) | NDPK BAKER'S YEAST Qty (µg) | NDPK HUMAN (erythrocyte) Qty (µg) | NDPK BOVINE (liver) Qty (µg) | % per NI OF THE PRODUCTS FORMED N | NMP | NDP | NTP | INCUBATION TIME min |
|---|---|---|---|---|---|---|---|---|---|---|
| | 10.4 | 7.4 | 0.75 | | | 2.9 | 2.6 | 12.6 | 82.9 | 20 |
| | 1.3 | 2.5 | 0.75 | | | 3.9 | 3.2 | 13.8 | 79.1 | 60 |
| | 10.4 | 7.4 | | 0.675 | | 2.0 | 6.2 | 90.3 | 1.5 | 20 |
| | " | " | | 6.75 | | 2.4 | 2.5 | 71.1 | 24.0 | 30 |
| | " | " | | | 0.5 | 2.2 | 6.5 | 78.4 | 12.9 | 20 |
| | " | " | | | 5 | 1.9 | 0.6 | 5.8 | 92.0 | 30 |
| ACV | 11.7 | 74 | | | | 20.0 | 26.0 | 54.0 | | 20 |
| | " | " | 1.5 | | | 19.0 | 13.0 | 60.0 | 8.0 | 20 |
| | " | " | 15 | | | 13.0 | 1.4 | 4.6 | 81.0 | 30 |
| | " | " | | 6.75 | | 18.0 | 1.8 | 80.0 | <0.4 | 30 |
| | " | " | | | 5 | 15.0 | 1.7 | 82.0 | 1.3 | 30 |

TABLE 3

Phosphorylation of GCV and of ACV by coupling or combination of the TK and GMPK enzymes

| Substrate | Fusion 200 µg | Mixture 2-865/H12/GMPK 133/66 µg (resp.) | Fusion 2 µg | Mixture wild type/GMPK 1.66/0.33 µg (resp.) | Mixture 2-865: H12/GMPK 1.66/0.33 µg (resp.) |
|---|---|---|---|---|---|
| GCV 100 µM | | | 8270** | 4660** | |
| GCV 50 µM | | | 4900** | | 5300** |
| ACV 100 µM | 18500** | 17260** | | | |

| | Fusion 50 µg | Mixture 2-865: H12/GMPK 33/17 µg (resp.) | Mixture wild type/GM 33/17 µg (resp.) |
|---|---|---|---|
| ACV 20 µM | 1220** | 2325** | 1045** |
| ACV 50 µM | 2920** | 3680** | 2390** |
| ACV 50 µM Incub 1 h | 6740** | 5890** | |

**pmmol of GCVDP formed

What is claimed is:

1. A composition of three nucleic acid vectors, comprising:
   (a) a first vector that comprises a nucleic acid that encodes a first enzyme that phosphorylates a nucleoside analogue to generate a monophosphate analog, wherein said nucleic acid is under the control of a transcriptional promoter;
   (b) a second vector that comprises a nucleic acid that encodes a second enzyme that phosphorylates the monophosphate analogue to generate a diphosphate analogue, wherein said nucleic acid is under the control of a transcriptional promoter; and
   (c) a third vector that comprises a nucleic acid that encodes third enzyme that phosphorylates the diphosphate analogue to generate a toxic triphosphate analogue, wherein said nucleic acid is under the control of a transcriptional promoter.

2. the composition according to claim 1, wherein said first enzyme is thymidine kinase.

3. The composition according to claim 1, wherein said second enzyme is a guanylate kinase.

4. The composition according to claim 1, wherein said third enzyme is a nucleoside diphosphate.

5. The composition according to claim 1, wherein the nucleic acid vectors are plasmid vectors.

6. The composition according to claim 1, wherein the nucleic acid vectors are viral vectors.

7. A composition comprising a first nucleic acid that expresses a thymidine kinase and a second nucleic acid that expresses a nucleoside diphosphate kinase (NDPK).

8. the composition according to claim 7, wherein the nucleoside diphosphate kinase is nonhuman.

9. The composition according to claim 8, wherein the nucleoside diphosphate kinase is selected from the group consisting of yeast NDPK and bovine NDPK.

10. The composition according to claim 7, further comprising a third nucleic acid that expresses a guanylate kinase.

11. The composition according to claim 10, wherein the third nucleic acid encodes a yeast guanylate kinase.

12. The composition according to claim 2 or 7, wherein the thymidine kinase is a viral thymidine kinase.

13. A vector comprising:
   (a) a first nucleic acid coding sequence encoding a thymidine kinase, wherein said first nucleic acid coding sequence is under the control of a first transcriptional promoter, and,
   (b) a second nucleic acid coding sequence encoding a nucleoside diphosphate kinase, wherein said second nucleic acid coding sequence is under the control of a second transcriptional promoter.

14. The vector according to claim 13, wherein the nucleoside diphosphate kinase is nonhuman.

15. The vector according to claim 14 wherein the nucleoside diphosphate kinase is a bovine nucleoside diphosphate kinase or a yeast nucleoside diphosphate kinase.

16. The vector according to claim 13, further comprising a nucleic acid coding sequence that expresses a guanylate kinase.

17. The vector according to claim 13, wherein the thymidine kinase is a viral thymidine kinase.

18. The vector according to claim 13, or 16 wherein the coding sequences are placed under the control of distinct promoters.

19. The vector according to claim 13, or 16, wherein the coding sequences form a polycistronic unit under the control of a single promoter.

20. A vector comprising:
   (a) a first nucleic acid coding sequence encoding a thymidine kinase, and
   (b) a second nucleic acid coding sequence encoding a nonhuman guanylate kinase, wherein the first nucleic acid coding sequence and the second nucleic acid coding sequence are coupled in-frame and express a protein possessing thymidine kinase and guanylate kinase activities.

21. The vector according to claim 13, which is a plasmid vector.

22. The vector according to claim 13, which is a viral vector.

23. A nucleic acid encoding a chimeric protein coupling a viral thymidine kinase and a guanylate kinase.

24. The nucleic acid according to claim 23, wherein the guanylate kinase is a yeast guanylate kinase.

25. A nucleic acid encoding a chimeric protein coupling a viral thymidine kinase and a nucleoside diphosphate kinase.

* * * * *